United States Patent [19]

Negoro et al.

[11] Patent Number: 5,258,382
[45] Date of Patent: Nov. 2, 1993

[54] TETRAHYDROPYRROLO[1,2-A]PYRAZINE-4-SPIRO-3'-PYRROLIDINE DERIVATIVES, PROCESSES FOR THE PREPARATION THEREOF AND PHARMACEUTICAL COMPOSITIONS CONTAINING THE SAME

[75] Inventors: Toshiyuki Negoro, Osaka; Makoto Murata, Hirakata; Shozo Ueda, Nara; Buichi Fujitani, Sakai; Yoshiyuki Ono, Kyoto, all of Japan

[73] Assignee: Dainippon Pharmaceutical Co., Ltd., Osaka, Japan

[21] Appl. No.: 901,029

[22] Filed: Jun. 19, 1992

[30] Foreign Application Priority Data

Jun. 26, 1991 [JP] Japan .................... 3-183185

[51] Int. Cl.$^5$ ............... A61K 31/495; C07D 487/20
[52] U.S. Cl. ................................. 514/249; 544/231;
544/349; 548/518; 548/531; 548/561; 548/562;
558/393
[58] Field of Search .................. 544/231; 514/249

[56] References Cited

U.S. PATENT DOCUMENTS 4,855,298 8/1989 Yamada et al. ................. 544/231

FOREIGN PATENT DOCUMENTS 0147805 7/1985 European Pat. Off. .
0173497 3/1986 European Pat. Off. .
0365324 4/1990 European Pat. Off. .

OTHER PUBLICATIONS

Chemical Abstracts, vol. 82, No. 23 (Jun. 1975); Abstract 156398q Moritomo et al; p. 621.

Primary Examiner—Emily Bernhardt
Attorney, Agent, or Firm—Birch, Stewart, Kolasch & Birch

[57] ABSTRACT

Tetrahydropyrrolo[1,2-a]pyrazine-4-spiro-3'-pyrrolidine derivatives of the formula:

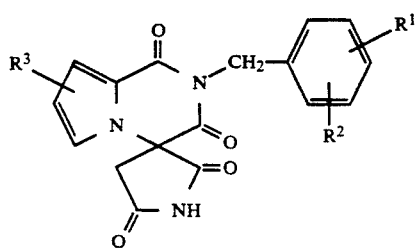

wherein $R^1$ and $R^2$ are independently hydrogen, halogen, trifluoromethyl, alkyl having 1 to 6 carbon atoms, alkoxy having 1 to 6 carbon atoms, or nitro, and $R^3$ is hydrogen, halogen or alkyl having 1 to 6 carbon atoms, and pharmaceutically acceptable salts thereof, processes for preparation thereof, and pharmaceutical composition containing the same. Said compounds and their salts show excellent aldose reductase inhibitory activity and are useful for the prevention and treatment of diabetic complications.

33 Claims, No Drawings

TETRAHYDROPYRROLO[1,2-A]PYRAZINE-4-SPIRO-3'-PYRROLIDINE DERIVATIVES, PROCESSES FOR THE PREPARATION THEREOF AND PHARMACEUTICAL COMPOSITIONS CONTAINING THE SAME

This invention relates to novel tetrahydropyrrolo[1,2-a]pyrazine-4-spiro-3'-pyrrolidine derivatives having an aldose reductase inhibitory activity, processes for the preparation thereof, a method of using the same, and pharmaceutical compositions containing said compound as an active ingredient.

PRIOR ART

European Patent 365324-A discloses spiro-isoquinoline-pyrrolidine tetrones of the formula:

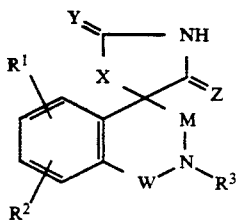

and analogues thereof wherein the fused benzene ring is replaced by a fused thiophen, pyridine or furan ring, wherein $R^1$ and $R^2$ are independently hydrogen, alkyl containing 1 to 6 carbon atoms, halogen, lower alkoxy containing 1 to 6 carbon atoms, trifluoromethyl, lower alkylthio wherein lower alkyl contains 1 to 6 carbon atoms, dialkylamino wherein alkyl contains 1 to 6 carbon atoms, nitro, aryl, or aryl(lower alkyl)oxy wherein aryl contains 6 to 10 carbon atoms and lower alkyl contains 1 to 6 carbon atoms; $R^3$ is hydrogen, lower alkyl containing 1 to 6 carbon atoms, aryl, aryl(lower alkyl) or halogen substituted aryl(lower alkyl) wherein aryl contains 6 to 10 carbon atoms and lower alkyl contains 1 to 6 carbon atoms, acyl or heterocyclic(lower alkyl) of structural formula:

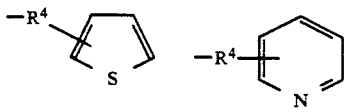

wherein $R^4$ is lower alkylene containing 1 to 3 carbon atoms; X is lower alkylene containing 1 to 3 carbon atoms, oxygen, sulfur or —NH—; Y and Z are independently oxygen or sulfur; M and W are independently carbonyl, thiocarbonyl, sulfonyl, sulfoxo or lower alkylene containing 1 to 2 carbon atoms, with the proviso that M and W are not both lower alkylene when X is —NH— and the pharmaceutically acceptable salts thereof. The compounds are disclosed to be useful as aldose reductase inhibitors for the prevention or treatment of complications associated with diabetes mellitus.

The compounds of this invention are clearly distinguished from the compounds of the above European patent in the chemical structure, that is, as is clear from the formula (I) disclosed hereinafter, the compounds (I) of this invention have a basic nucleus of pyrrolo[1,2-a]pyrazine ring which is clearly different from the basic nucleus of the above compounds of the European patent.

Diabetic patients have been symptomatically treated with insulin or oral hypoglycemic agents. However, none of these treatments is able to reinstate entirely normal glycemic condition, and complications associated with prolonged hyperglycemia, such as cataract, retinopathy, keratopathy, neuropathy and nephropathy, develop during long-term diabetic period. Therefore, the prevention of the initiation and progression of the diabetic complications are becoming one of the most important subjects of nowadays for the treatment of the diabetes mellitus.

The abnormality of polyol metabolic pathway is postulated to be a common biochemical link to the pathogenesis of various diabetic complications. Aldose reductase, the key enzyme of polyol pathway, catalyzes the conversion of glucose to sorbitol. The influx of glucose into target tissues of diabetic complications (e.g. blood vessels, peripheral nerves, lenses and kidneys) is greater in diabetics as compared with that in normal tissues. The increase in glucose activates aldose reductase and thereby accelerates sorbitol formation, resulting in an accumulation of sorbitol in these tissues. The intracellular accumulation of sorbitol is considered to produce a hyperosmotic effect which results in an accumulation of fluid, which, in turn, produces cellular damage and causes pathogenesis of diabetic complications [P. F. Kador et al., Ann. Rev. Pharmacol. Toxicol., 25, 691–714 (1985)]. Accordingly, it is considered that a compound having aldose reductase inhibitory activity will be effective for the prevention and treatment of diabetic complications and many researchers in the world have investigated various types of compounds for developing a new aldose reductase inhibitory agent. Until now, only two aldose reductase inhibitory agents, N-[[6-methoxy-5-(trifluoromethyl)-1-naphthalenyl]thioxomethyl]-N-methylglycine [generic name: tolrestat, cf. Merck Index, 11th Ed., 9451 (1989)] and (E,E)-5-(2-methyl-3-phenyl-2-propenylidene) 4-oxo-2-thioxo-3-thiazolidineacetic acid [generic name: epalrestat, cf. Merck Index, 11th Ed., 3556 (1989)] are commercially available in some countries. However, these compounds do not have necessarily sufficient activity [cf. the experiments disclosed hereinafter, and N. Simard-Duquesne, et. al., Metab. Clin. Exp., 34, 885–892 (1985)]. Thus, there has been sought a new compound having more potent aldose reductase inhibitory activity with less toxicity.

BRIEF DESCRIPTION OF THE INVENTION

The present inventors have intensively investigated to find a desired new compound having superior aldose reductase inhibitory activity with less toxicity and as a result have found that some compounds having a tetrahydropyrrolo[1,2-a]pyrazine-4-spiro-3'-pyrrolidine nucleus possess the desired properties.

Thus, an object of the invention is to provide novel tetrahydropyrrolo[1,2-a]pyrazine-4-spiro-3'-pyrrolidine derivatives having excellent aldose reductase inhibitory activity. Another object of the invention is to provide processes for the preparation of the new compounds. A further object of the invention is to provide use of the compounds for the prevention and treatment of diabetic complications. Still further object of the invention is to provide pharmaceutical compositions containing as an active ingredient said compound which are useful for the prevention and treatment of diabetic complications.

These and other objects and advantages of the invention will be apparent to those skilled in the art from the following description.

DETAILED DESCRIPTION OF THE INVENTION

The tetrahydropyrrolo[1,2-a]pyrazine-4-spiro-3'-pyrrolidine derivatives of this invention are compounds of the formula:

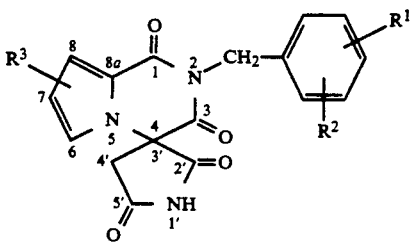

wherein $R^1$ and $R^2$ are independently hydrogen, halogen, trifluoromethyl, alkyl having 1 to 6 carbon atoms, alkoxy having 1 to 6 carbon atoms, or nitro, and $R^3$ is hydrogen, halogen or alkyl having 1 to 6 carbon atoms, and pharmaceutically acceptable salts thereof.

The pharmaceutically acceptable salts of the compounds (I) include salts with inorganic bases (e.g. sodium, potassium, and ammonium) and salts with organic bases (e.g. isopropylamine, diethylamine, ethanolamine, triethanolamine, piperidine, and lysine).

The compounds (I) and their salts may be present in the form of a hydrate or a solvate, and these hydrate and solvate are also included in this invention.

Besides, the compounds (I) contain at least one asymmetric carbon atom, that is, the spiro carbon atom at 3'-position of the pyrrolidine ring, and hence, various stereoisomers may be present. These stereoisomers and their mixture and racemic compounds are also included in this invention. In case of the compounds of the formula (I) wherein $R^1$, $R^2$ and $R^3$ are all a group containing no asymmetric carbon atom, one enantiomer has more potent aldose reductase inhibitory activity than the other enantiomer.

Through the specification and claims, "halogen" denotes fluorine, chlorine, bromine and iodine. "Alkyl" denotes, for example, methyl, ethyl, propyl, isopropyl, butyl, isobutyl, pentyl, and hexyl, preferably alkyl having 1 to 3 carbon atoms.

"Alkoxy" denotes, for example, methoxy, ethoxy, propoxy, isopropoxy, butoxy, isobutoxy, pentyloxy, and hexyloxy, preferably alkoxy having 1 to 3 carbon atoms.

The group of the formula:

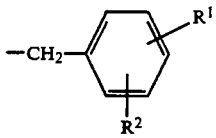

includes, for example, benzyl, 2-bromobenzyl, 2-chlorobenzyl, 2-fluorobenzyl, 3-bromobenzyl, 3-chlorobenzyl, 3-fluorobenzyl, 4-bromobenzyl, 4-chlorobenzyl, 4-fluorobenzyl, 4-iodobenzyl, 4-bromo-3-chlorobenzyl, 4-bromo-2-fluorobenzyl, 4-chloro-2-fluorobenzyl, 2,4-dichlorobenzyl, 3,4-dichlorobenzyl, 3,5-dichlorobenzyl, 2,4-dibromobenzyl, 3,4-dibromobenzyl, 3,5-dibromobenzyl, 2,4-difluorobenzyl, 2-fluoro-4-iodobenzyl, 4-trifluoromethylbenzyl, 4-methylbenzyl, 4-methoxybenzyl, 3,4-dimethoxybenzyl, 2,4-dimethoxybenzyl, and 4-nitrobenzyl.

Preferred compounds are compounds of the formula (I) wherein $R^3$ is hydrogen, halogen, or 7-methyl, and pharmaceutically acceptable salts thereof. More preferred compounds are compounds of the formula (I) wherein $R^1$ and $R^2$ are independently hydrogen or halogen and $R^3$ is hydrogen, halogen, or 7-methyl, and pharmaceutically acceptable salts thereof. Other more preferred compounds are compounds of the formula (I) wherein $R^1$ is alkyl having 1 to 3 carbon atoms or alkoxy having 1 to 3 carbon atoms, and $R^3$ is hydrogen, halogen, or 7-methyl, and pharmaceutically acceptable salts thereof. Particularly preferred compounds are compounds of the formula (I) wherein $R^1$ is hydrogen or halogen, $R^2$ is halogen and $R^3$ is hydrogen.

Preferred stereoisomers of the compounds (I) are racemic compounds and enantiomers thereof having more potent aldose reductase inhibitory activity compared with the other enantiomers.

Specific examples of the particularly preferred compounds are the following compounds and enantiomers thereof having more potent aldose reductase inhibitory activity compared with the other enantiomers:

2-(4-bromo-2-fluorobenzyl)-[1,2,3,4-tetrahydropyrrolo[1,2-a]pyrazine-4-spiro-3'-pyrrolidine]-1,2',3,5'-tetrone, 2-(3,4-dichlorobenzyl)-[1,2,3,4-tetrahydropyrrolo[1,2-a]pyrazine-4-spiro-3'-pyrrolidine]-1,2',3,5'-tetrone, 2-(4-bromobenzyl)-[1,2,3,4-tetrahydropyrrolo[1,2-a]pyrazine-4-spiro-3'-pyrrolidine]-1,2',3,5'-tetrone, and 2-(4 chloro 2-fluorobenzyl)-[1,2,3,4-tetrahydropyrrolo[1,2-a]pyrazine-4-spiro-3'-pyrrolidine]-1,2',3,5'-tetrone.

The most preferred compound is a compound of the formula (I'):

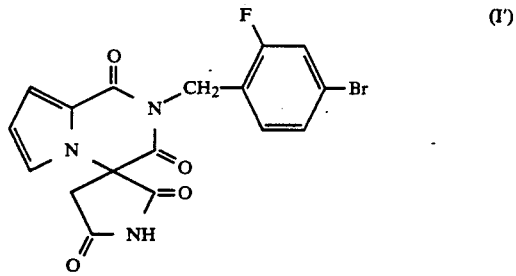

Specific examples of said most preferred compounds are as follows:

2-(4-bromo-2-fluorobenzyl)-[1,2,3,4-tetrahydropyrrolo[1,2-a]pyrazine-4-spiro-3'-pyrrolidine]-1,2',3,5'-tetrone, and an enantiomer of 2-(4-bromo-2-fluorobenzyl)-[1,2,3,4-tetrahydropyrrolo[1,2-a]pyrazine-4-spiro-3'-pyrrolidine]-1,2',3,5'-tetrone having the following specific rotation: $[\alpha]_D^{27.5} = +1.96°$ (c=1.02, ethyl acetate); $[\alpha]_D^{28} = -7.6°$ (c=1.02, methanol); and $[\alpha]_{405}^{28} = -33.0°$ (c=1.02, methanol).

The following compounds and enantiomers thereof are also enumerated as examples of compounds of the formula (I) as well as the compounds of working examples given hereinafter.

2-(2-fluoro-4-iodobenzyl)-[1,2,3,4-tetrahydropyrrolo[1,2-a]pyrazine-4-spiro-3'-pyrrolidine]-1,2',3,5'-tetrone, 2-(4-bromo-3-chlorobenzyl)-[1,2,3,4-tetrahydropyrrolo[1,2-a]pyrazine-4-spiro-3'-pyrrolidine]-1,2',3,5'-tetrone, 2-(2,4-dibromobenzyl)-[1,2,3,4-tetrahydropyrrolo[1,2-a]pyrazine-4-spiro-3'-pyrrolidine]-1,2',3,5'-tetrone, 2-(3,4-dibromobenzyl)-[1,2,3,4-tetrahydropyrrolo[1,2-a]pyrazine-4-spiro-3'-pyrrolidine]-1,2',3,5'-tetrone, 2-(3,5-dibromobenzyl)-[1,2,3,4-tetrahydropyrrolo[1,2-a]pyrazine-4-spiro-3'-pyrrolidine]-1,2',3,5'-tetrone, and 2-(4-bromo-2-fluorobenzyl)-7-methyl-[1,2,3,4-tetrahydropyrrolo[1,2-a]pyrazine-4-spiro-3'-pyrrolidine]-1,2',3,5'-tetrone.

The compounds of this invention may be prepared, for example, by the following processes.

Process (a)

The compounds (I) can be prepared by reacting a compound of the formula (II):

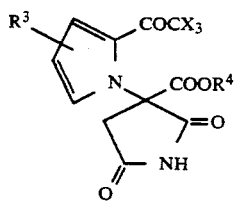

(II)

wherein $R^3$ is as defined above, and $R^4$ is a carboxy-protecting group, and X is halogen, with a compound of the formula (III):

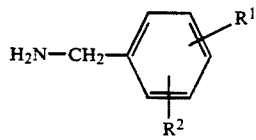

(III)

wherein $R^1$ and $R^2$ are as defined above.

The "carboxy-protecting group" for $R^4$ in the above compound (II) means all conventional protecting groups capable of being easily removed by conventional means such as hydrolysis and hydrogenolysis which are usually used in the field of peptide synthesis. Suitable examples of the protecting groups removable by hydrolysis are lower alkyl groups such as methyl, ethyl, and propyl, and suitable examples of the protecting groups removable by hydrogenolysis are benzyl, 4-methoxybenzyl, and 4-nitrobenzyl. The hydrogenolysis includes various means such as catalytic reduction and catalytic transfer hydrogenation.

The reaction of the compound (II) and the compound (III) is usually carried out in a solvent which does not adversely influence the reaction. Suitable solvent may be selected in accordance with, for example, the kinds of the starting compounds, and includes, for example, aromatic hydrocarbons such as benzene and toluene; halogenated hydrocarbons such as dichloromethane and chloroform; ethers such as tetrahydrofuran and dioxane; and dimethylformamide. These solvents may be used alone or in combination of two or more thereof. The above reaction is preferably carried out in the presence of a basic substance, which includes, for example, organic bases such as triethylamine, tributylamine, diisopropylethylamine, N-methylmorpholine, pyridine, and N,N-dimethylaniline; and inorganic bases such as alkali metal carbonates (e.g. sodium carbonate and potassium carbonate), or alkali metal hydrogen carbonates (e.g. sodium hydrogen carbonate and potassium hydrogen carbonate). Alternatively, an excess amount of the compound (III) may be used instead of using the specific basic substance. The reaction temperature may vary depending, for example, on the kinds of the starting compounds, but is usually in the range of about 0° C. to about 100° C., preferably in the range of about 25° C. to about 70° C. The compound (III) may also be used in the form of an acid addition salt, which is converted into a free base in the reaction system.

Some of the compounds (III) are commercially available and others can be prepared by a process known per se. The compounds (II) are novel and can be prepared, for example, by the process as shown in the following Reaction Scheme-I.

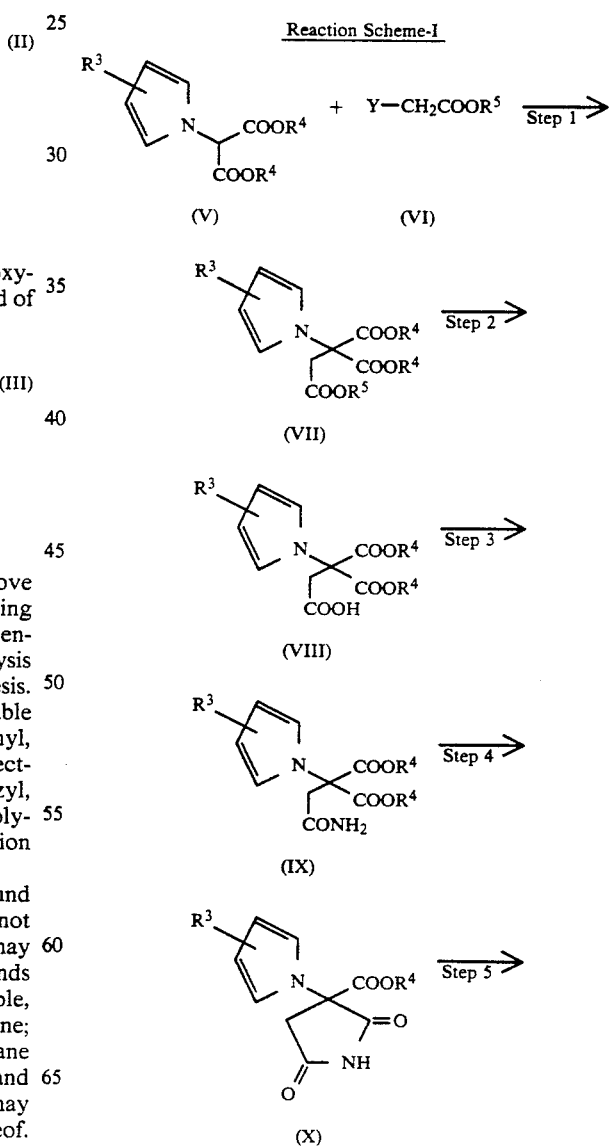

-continued
Reaction Scheme-I

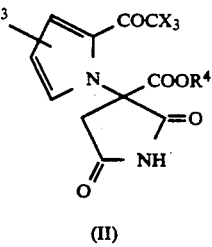

(II)

wherein $R^3$, $R^4$ and X are as defined above, $R^5$ is tert-butyl or a protecting group removable by hydrogenolysis, and Y is halogen, provided that when $R^4$ is a protecting group removable by hydrogenolysis, $R^5$ is tert-butyl.

Each step in the above Reaction Scheme-I is carried out as follows.

(Step 1)

The compound (V) can be prepared, for example, by the method as disclosed in J. Med. Chem., 21, 962-964 (1978).

The reaction of the compound (V) and the compound (VI) is usually carried out in an appropriate solvent in the presence of a basic substance. The solvent includes, for example, cyclohexane, benzene, toluene, xylene, tetrahydrofuran, dioxane, methanol, ethanol, isopropyl alcohol, pyridine, and dimethylformamide. The basic substance includes, for example, alkali metals (e.g. lithium, sodium, and potassium), alkali metal hydrides (e.g. sodium hydride), alkali metal hydroxides (e.g. sodium hydroxide and potassium hydroxide), alkali metal carbonates (e.g. sodium carbonate and potassium carbonate), alkali metal hydrogen carbonates (e.g. sodium hydrogen carbonate and potassium hydrogen carbonate), and alkali metal alkoxides (e.g. sodium methoxide, sodium ethoxide, and potassium tert-butoxide). The reaction is usually carried our at a temperature of about $-10°$ C. to about 150° C.

(Step 2)

The "protecting group removable by hydrogenolysis" for $R^5$ in the formula (VII) means a group capable of being easily removed by catalytic reduction or catalytic transfer hydrogenation, and includes, for example, benzyl, 4-nitrobenzyl, and 4-methoxybenzyl.

The compound of the formula (VII) wherein $R^5$ is tert-butyl can be converted into the compound (VIII) by treating with trifluoroacetic acid in an appropriate solvent such as dichloromethane or chloroform. The reaction is usually carried out at a temperature of about 25° C. to about 50° C.

The compound of the formula (VII) wherein $R^5$ is a protecting group removable by hydrogenolysis can be converted into the compound (VIII) by hydrogenating in the presence of a catalyst such as Raney nickel or palladium-carbon in an appropriate solvent, or alternatively by reacting with a hydrogen donor (e.g. ammonium formate or cyclohexene) in the presence of a catalyst such as palladium-carbon in an appropriate solvent. The solvent includes, for example, water, methanol, ethanol, acetic acid, dioxane, and tetrahydrofuran. The reaction is usually carried out at a temperature of about 25° C. to about 80° C. at atmospheric pressure or under pressure.

(Step 3)

The compound (VIII) or a reactive derivative at the carboxyl group thereof is reacted with ammonia under a conventional condition suitable for amidation reaction to give the compound (IX).

The reactive derivative at the carboxyl group of the compound (VIII) includes acid chlorides and active esters (e.g. N-hydroxysuccinimide ester and N-hydroxyphthalimide ester). When the compound (VIII) itself is used, the reaction is usually carried out in the presence of a conventional condensation agent, such as dicyclohexylcarbodiimide, 1-ethyl-3-(3-dimethylaminopropyl)-carbodiimide hydrochloride, or N,N'-carbonyldiimidazole. The reaction is usually carried out in an appropriate solvent, such as benzene, toluene, dichloromethane, chloroform, tetrahydrofuran, dioxane, acetonitrile, or dimethylformamide, at a temperature of about 0° C. to about 150° C.

(Step 4)

The compound (IX) obtained in the above step 3 is subjected to cyclization reaction in the presence of a basic substance to give the compound (X). The reaction may be carried out by using the same basic substance and solvent as used in Process (b) disclosed hereinafter. The reaction is usually carried our at a temperature of about $-20°$ C. to about 60° C.

(Step 5)

The compound (X) obtained in the above step 4 is reacted with a trihalogenoacetic halide of the formula: $CX_3COZ$ (wherein X is as defined above, and Z is a halogen such as chlorine or bromine) or a trihalogenoacetic anhydride of the formula: $(CX_3CO)_2O$ (wherein X is as defined above) in the absence or presence of an appropriate solvent to give the compound (II). The solvent includes, for example, dichloromethane, chloroform, diethyl ether, tetrahydrofuran, and dioxane. The reaction may be carried out in the presence of a basic substance, such as organic bases (e.g. triethylamine, pyridine, and N,N-dimethylaniline), or inorganic bases (e.g. sodium carbonate, potassium carbonate, sodium hydrogen carbonate, and potassium hydrogen carbonate). The reaction temperature is in the range of about 25° C. to about 150° C.

In the above Process (a), when the compound (II) and/or the compound (III) has one or two asymmetric carbon atoms, the configuration as to the asymmetric carbon atom(s) is retained in the final compound (I). That is, from the compound (II) and the compound (III) in the form of racemic compound, there is obtained the compound (I) in the form of racemic compound.

The enantiomers of the compounds of the formula (II) wherein $R^3$ is hydrogen can be prepared, for example, by separating the product (XV) obtained in the step 3 in the following Reaction Scheme II into two kinds of enantiomers, converting each enantiomer into the compound (X') in the step 4, followed by subjecting to the reaction as in the step 5 in the above Reaction Scheme-I. The resolution of the compound (XV) into each enantiomer can be carried out, for example, by forming diastereomeric salts thereof with an optically active acid by a conventional method, separating into two kinds of diastereomeric salts and then converting each diastereomeric salt into the corresponding free base. The optically active acid used as a resolving agent in the above resolution includes, for example, (+)-camphoric acid, (1S)-(+)- or (1R)-(−)-camphorsulfonic acid, L-(+)- or D-(−)-tartaric acid, L- or D-pyroglutamic acid, (S)-(−)- or (R)-(+)-malic acid, (S)-(+)- or (R)-(−)-1,1'-binaphthyl-2,2'-diyl hydrogen phosphate, (−)- or (+)-2'-nitrotartranilic acid, D-(+)-tartranilic acid, (−)-dibenzoyl-L-tartaric acid, (+)-dibenzoyl-D-tartaric acid, and (−)-diacetyl-L-tartaric acid.

Reaction Scheme-II

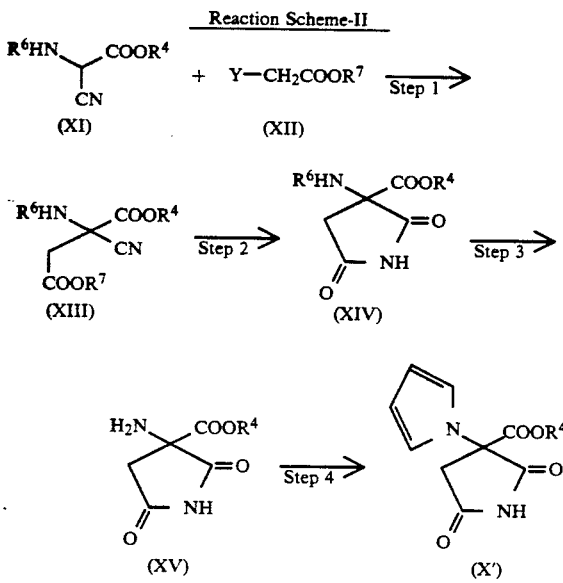

wherein $R^4$ is as defined above, $R^6$ is benzyloxycarbonyl or tert-butoxycarbonyl, and $R^7$ is a carboxy-protecting group, provided that when $R^6$ is benzyloxycarbonyl, $R^4$ is a protecting group removable by hydrolysis.

Each step in the above Reaction Scheme-II is carried out as follows.

(Step 1)

The compound (XI) can be prepared by introducing a protecting group on the amino group of 2-amino-2-cyanoacetic acid ester by a conventional method, said 2-amino-2-cyanoacetic acid ester being prepared by the method as disclosed in Chem. Ind. (London), 1980, 541–542.

The reaction of the compound (XI) and the compound (XII) is carried out in the same manner as described in the step 1 in Reaction Scheme-I.

(Step 2)

The conversion of the compound (XIII) into the compound (XIV) can be carried out by a known method which is usually used in the hydrolysis of nitrile to amide, for example, the method as disclosed in Synthesis, 1980, 243–244.

(Step 3)

The conversion of the compound (XIV) into the compound (XV) can be carried out in the same manner as described in the step 2 in Reaction Scheme-I.

(Step 4)

The conversion of the compound (XV) into the compound (X') can be carried out by a known method, for example, the method as disclosed in J. Med. Chem., 21, 962–964 (1978).

Process (b)

The compounds (I) of this invention can also be prepared by cyclizing a compound of the formula (IV):

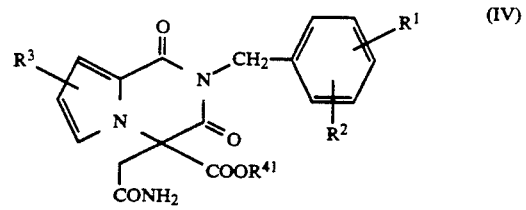

wherein $R^1$, $R^2$ and $R^3$ are as defined above, and $R^{41}$ is a carboxy-protecting group or an alkyl residue of an optically active alcohol, provided that when $R^{41}$ is an alkyl residue of an optically active alcohol, the configuration at the carbon atom at 4-position of tetrahydropyrrolo[1,2-a]pyrazine ring is S or R. The cyclization is carried out in the presence of a basic substance.

The alkyl residue of an optically active alcohol for $R^{41}$ in the above formula (IV) means a group derived from an optically active alcohol having one or more asymmetric carbon atoms by removing the hydroxy group therefrom, and includes, for example, (−)- or (+)-menthyl, (−)- or (+)-1-phenylethyl, (−)- or (+)-2-butyl, and (−)-bornyl.

The cyclization reaction is usually carried out in an appropriate solvent. Suitable examples of the solvent are aromatic hydrocarbons such as benzene and toluene; ethers such as diethyl ether, tetrahydrofuran, and dioxane; and dimethylformamide. The basic substance used therein includes, for example, alkali metals (e.g. lithium, sodium, and potassium), alkaline earth metals (e.g. calcium), alkali metal hydrides (e.g. sodium hydride), alkaline earth metal hydrides (e.g. calcium hydride), alkali metal hydroxides (e.g. sodium hydroxide and potassium hydroxide), alkali metal carbonates (e.g. sodium carbonate and potassium carbonate), alkali metal hydrogen carbonates (e.g. sodium hydrogen carbonate and potassium hydrogen carbonate), and alkali metal alkoxides (e.g. sodium methoxide, sodium ethoxide, and potassium tert-butoxide), organic lithium compounds (e.g. lithium bis(trimethylsilyl)amide, lithium diisopropylamide, and n-butyllithium), organic acid salts (e.g. sodium acetate), and organic bases (e.g. triethylamine, pyridine, lutidine, and 1,8-diazabicyclo[5.4.0]-undecane). The reaction is usually carried out at a temperature of about −78° C. to about 25° C., preferably about −78° C. to about −20° C.

The compounds of the formula (IV) wherein $R^{41}$ is the same as $R^4$, i.e. a carboxy-protecting group, are novel compounds and can be prepared, for example, by the process as shown in the following Reaction Scheme-III.

Reaction Scheme-III

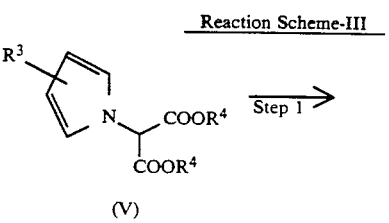

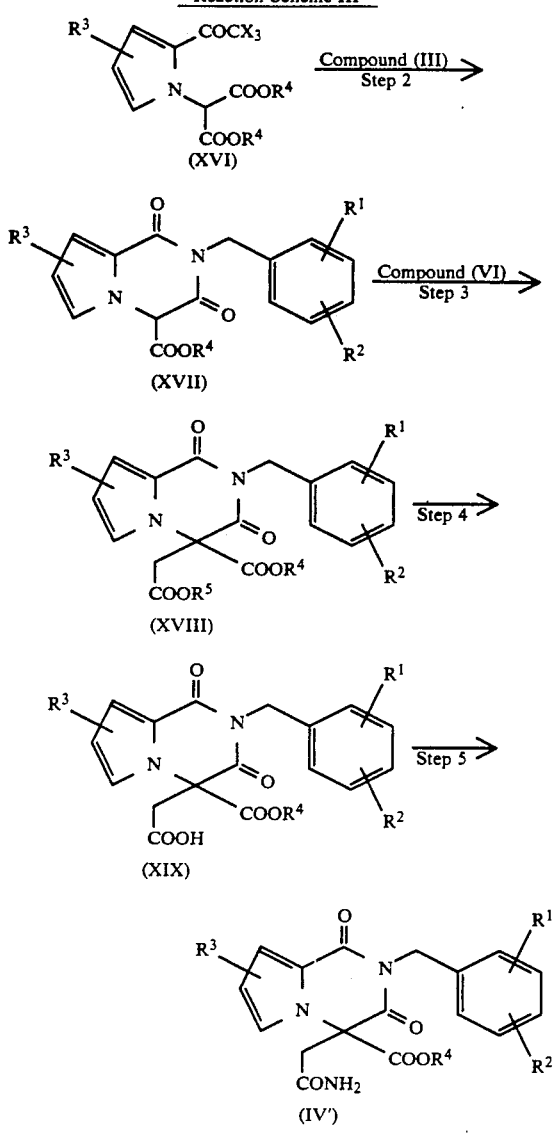

wherein $R^1$, $R^2$, $R^3$, $R^4$ and $R^5$ are as defined above, provided that when $R^4$ is a protecting group removable by hydrogenolysis, $R^5$ is tert-butyl.

Each step in the above Reaction Scheme-III is carried out as follows.

(Step 1)

This step can be carried out in the same manner as described in the step 5 in Reaction Scheme-I.

(Step 2)

This step can be carried out in the same manner as described in the above Process (a), preferably in an inert atmosphere.

(Step 3)

The compound (XVII) and the compound (VI) are reacted in the same manner as described in the step 1 in Reaction Scheme-I to give the compound (XVIII). The reaction is preferably carried out in an inert atmosphere.

(Step 4)

The compound (XVIII) can be converted into the compound (XIX) in the same manner as described in the step 2 in Reaction Scheme-I.

(Step 5)

The compound (XIX) or a reactive derivative at the carboxyl group thereof is reacted with ammonia in the same manner as described in the step 3 in Reaction Scheme-I to give the compound (IV').

The compounds of the formula (IV) wherein $R^{41}$ is an alkyl residue of an optically active alcohol are novel compounds and can be prepared, for example, by the process as shown in the following Reaction Scheme-IV.

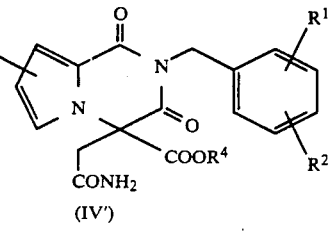

Reaction Scheme-IV

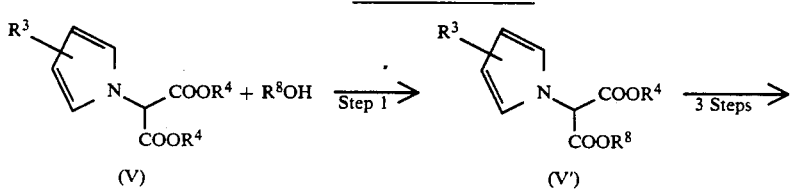

-continued
Reaction Scheme-IV

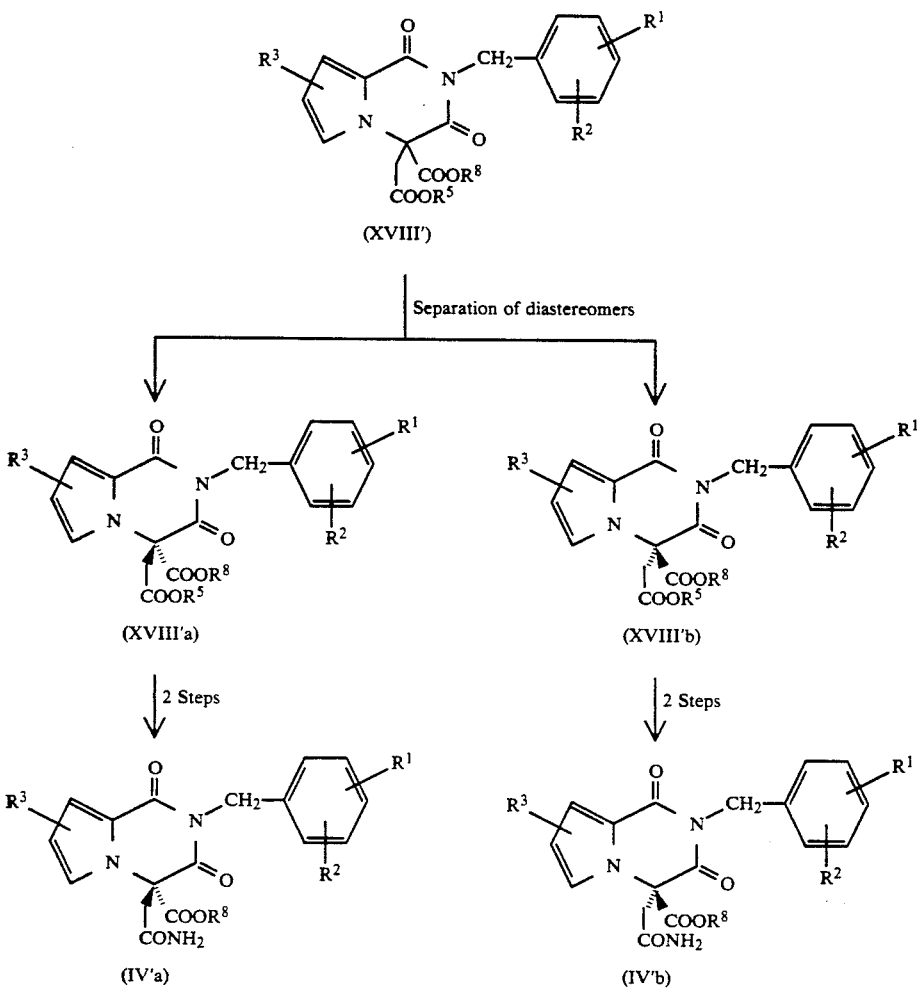

wherein $R^1$, $R^2$, $R^3$, $R^4$ and $R^5$ are as defined above, and $R^8$ is an alkyl residue of an optically active alcohol.

Each step in the above Reaction Scheme-IV is carried our as follows.

(Step 1)

The reaction of the compound (V) and a compound of the formula: $R^8OH$ (wherein $R^8$ is as defined above) is usually carried out in the presence of a catalyst. The catalyst includes those used usually in ester exchange reaction, for example, sulfuric acid, benzenesulfonic acid, p-toluenesulfonic acid, sodium, potassium, sodium methoxide, and tetraethyl titanate. The reaction is usually carried out at a temperature of about 25° C. to about 200° C., preferably about 100° C. to about 200° C.

[Conversion of the compound (V') into the compound (XVIII')]

The conversion can be carried out in the same manner as described in the steps 1 to 3 in Reaction Scheme-III.

[Separation of the compound (XVIII ) into each diastereomer]

The compound (XVIII') is obtained as a mixture of two kinds of diastereomers in the preceding step. This compound can be separated into two kinds of diastereomers, i.e. the compound (XVIII'a) and the compound (XVIII'b), by conventional methods, such as fractional crystallization and column chromatography.

[Production of the compound (IV'a) and the compound (IV'b)]

The conversion of the compound (XVIII'a) and the compound (XVIII'b) into the compound (IV'a) and the compound (IV'b), respectively, can be carried out in the same manner as described in the steps 4 and 5 in Reaction Scheme-III.

The products prepared by the above processes can be isolated and purified by conventional methods, such as chromatography, recrystallization, or reprecipitation.

The compounds of the formula (I) wherein $R^3$ is hydrogen can be converted into the corresponding compounds wherein $R^3$ is halogen by reacting with a halogenating agent such as a halogen (e.g. chlorine or bromine) or sulfuryl chloride. The reaction is preferably carried out in an appropriate solvent, such as carbon disulfide, dichloromethane, chloroform, 1,2-dichloroethane, or dimethylformamide, at a temperature of about −20° C. to about 100° C. The reaction may also be carried out in the presence of aluminum chloride.

When the compound (II) in which $R^3$ is halogen, which is prepared by halogenating a compound (II) in which $R^3$ is hydrogen, is used as a starting compound in Process (a), the halogen can be introduced at a position different from that of the product obtained by halogenation of the compound (I) in which $R^3$ is hydrogen as mentioned above. The halogenation of a compound (II) in which $R^3$ is hydrogen can be carried out in a conventional manner as shown in Reference Examples 22 and 23 hereinafter.

The compounds of the formula (I) can be converted into their salts by treating with inorganic or organic bases in a usual manner. Suitable examples of the inorganic and organic bases are hydroxides, carbonates or hydrogen carbonates of alkali metal (e.g. sodium or potassium), ammonium hydroxide, isopropylamine, diethylamine, ethanolamine, piperidine, and lysine. This reaction is usually carried out at a temperature of about 0° C. to about 25° C. in an appropriate solvent. The solvent includes, for example, lower alcohols (e.g. methanol, ethanol, and isopropyl alcohol), ethyl acetate, acetonitrile, dioxane, and toluene, or a mixture thereof.

The pharmacological activities of the compounds of this invention are illustrated by the following experiments, which were carried out for the representative compounds of this invention.

The following compounds were used as a reference compound:

Epalrestat: an aldose reductase inhibitor commercially available in Japan, and (±)-Sorbinil: an aldose reductase inhibitor whose chemical name is 6-fluoro-2,3-dihydrospiro[4H-1-benzopyran-4,4'-imidazolidine]-2',5'-dione [cf. Merck Index, 11th Ed., 8679 (1989)].

Test 1 Aldose reductase inhibitory activity (in vitro)

This test was carried out according to the method of S. Hayman and J. H. Kinoshita [J. Biol. Chem., 240, 877-882 (1965)].

Preparation of crude enzyme solution

Lenses isolated from porcine eyes (Tokyo Sibaura Zouki Co., Ltd., Japan) were homogenized with 5 mM phosphate buffer (pH 7.4) containing 2 mM mercaptoethanol, and centrifuged at 10,200 g for 10 minutes. The supernatant was sequentially precipitated with ammonium sulfate at 30%, 40% and 60% saturation. The precipitate at 60% saturation was dissolved in a homogenizing buffer and used as a crude enzyme preparation. The unit of enzyme activity was defined as the amount of enzyme which oxidized 1 μmoles of NADPH/minute under the following assay condition.

Enzyme assay

The standard reaction mixture was composed of 100 mM phosphate buffer (pH 6.5), 0.2 mM NADPH, 1.5 mM D,L-glyceraldehyde, 0.4M lithium sulfate, enzyme solution (7.0 mU/ml) and test compounds at various concentrations. The reaction mixture was incubated at 37° C., and the decrease in absorbance at 340 nm was monitored by a spectrophotometer (Hitachi 150-20). The enzyme activity was calculated based upon the rate of decrease in the absorbance over a period of 1 minute from 1 minute after the onset of the enzyme reaction. The concentration of compounds required for 50% inhibition of enzyme activity ($IC_{50}$) was estimated from graphs of the log concentration—response curve. The results are shown in Table 1.

TABLE 1

| Aldose reductase inhibitory activity | | | |
|---|---|---|---|
| Test compound | $IC_{50}$ (μM) | Test compound | $IC_{50}$ (μM) |
| 1* | 0.050 | 13 | 0.11 |
| 2 | 0.033 | 15 | 0.11 |
| 3 | 0.099 | 16 | 0.041 |
| 4 | 0.061 | 17 | 0.052 |
| 5 | 0.031 | 18 | 0.037 |
| 6 | 0.12 | 19 | 0.050 |
| 7 | 0.033 | 20 | 0.10 |
| 8 | 0.047 | 22 | 0.039 |
| 9 | 0.080 | 24 | 0.023 |
| 10 | 0.072 | 26 | 0.040 |
| 11 | 0.052 | 27 | 0.035 |
| 12 | 0.046 | | |
| Epalrestat | 0.073 | (±)-Sorbinil | 3.8 |

*The numbers of test compounds correspond to the Example Nos., and for example, Test compound 1 is the compound obtained in Example 1. All test compounds in the above table and also the other table hereinafter are indicated in the same way.

As shown in Table 1, the compounds of this invention were remarkably more potent than (±)-sorbinil in the aldose reductase inhibitory activity, and most of them were equipotent to or more potent than epalrestat.

Test 2 Inhibitory activity on sorbitol accumulation (in vivo)

Male Wistar rats (200-250 g) were used in groups of 4 animals each. The rats were made diabetic by single i.v. injection of streptozotocin (40 mg/kg) freshly dissolved in physiological saline.

From one week after the induction of diabetes, the rats were orally given test compounds, suspended in 0.5% tragacanth solution, once a day for 5 days. The sciatic nerves were isolated from the rats 4 hours after the final administration, and sorbitol contents in the nerve tissues were determined by the enzymatic fluorospectrophotometric method of R. S. Clement et al. [Science, 166, 1007-1008 (1969)] using sorbitol dehydrogenase from sheep liver as an enzyme preparation. The activity of test compounds was expressed as the inhibition percent of sorbitol accumulation ar given doses, which was calculated according to the following equation.

Inhibition $\% = (S-T)/(S-N) \times 100$

S: Sorbitol content in sciatic nerve from diabetic control

T: Sorbitol content in sciatic nerve from diabetic rats given test compounds

N: Sorbitol content in sciatic nerve from normal rats.

The results are shown in Table 2.

TABLE 2

| Inhibitory activity on sorbitol accumulation | | |
|---|---|---|
| Test compound | Dose (mg/kg/day) | Inhibition (%) |
| 1 | 30 | 114.6 |
|   | 1.0 | 104.7 |
| 2 | 30 | 97.1 |
|   | 3.0 | 30.5 |
| 3 | 30 | 69.1 |
| 4 | 10 | 73.5 |
|   | 1.0 | 47.2 |
| 5 | 30 | 99.4 |
|   | 3.0 | 44.2 |
| 6 | 30 | 55.8 |
| 7 | 30 | 104.6 |
|   | 3.0 | 69.7 |
| 8 | 3.0 | 104.7 |
| 10 | 30 | 98.0 |
|   | 3.0 | 33.3 |

TABLE 2-continued

| Inhibitory activity on sorbitol accumulation | | |
|---|---|---|
| Test compound | Dose (mg/kg/day) | Inhibition (%) |
| 11 | 30 | 65.8 |
| 15 | 30 | 102.2 |
|  | 3.0 | 7.4 |
| 16 | 1.0 | 61.0 |
| 22 | 1.0 | 107.3 |
|  | 0.3 | 77.6 |
| 24 | 30 | 111.8 |
|  | 1.0 | 70.9 |
| Epalrestat | 200 | 5.7 |
| (±)-Sorbinil | 30 | 106.9 |
|  | 3.0 | 60.7 |

As shown in Table 2, the compounds of the present invention were remarkably more potent than epalrestat in inhibitory activity on sorbitol accumulation. The compounds of Examples 1, 4, 5, 7, 8, 16, 22 and 24 were equipotent to or more potent than (±)-sorbinil. Further, the effect of the compounds of Examples 1 (21) and 22 was long-lasting.

Test 3 Acute toxicity

Male ddY mice (18–25 g) were used in groups of 5 animals each. The compounds of Examples 1 (21) and 22, suspended in 0.5% tragacanth solution, were orally administered at a dose of 1 g/kg to the animals. The mortality was observed for 7 days after the administration. None of the mice died during this period.

As is clear from the above experimental results, the compounds of the formula (I) have excellent aldose reductase inhibitory activity with less toxicity, and hence, they are useful as an agent for treating diabetic complications. They can be used in the prevention and treatment of various complications associated with diabetes mellitus in mammals including human being, such as cataract, retinopathy, keratopathy, neuropathy or nephropathy.

The compounds of the invention can be administered by any route, such as oral route, parenteral route, intrarectal route, or topical route, but preferably by oral route. The clinical dose of the compounds of the invention may vary in accordance with, for example, the kinds of the compounds, administration routes, severity of the diseases, and ages of the patients, but is usually in the range of 0.01 to 20 mg/kg/day, preferably 0.05 to 10 mg/kg/day, in human.

The compounds of the invention are usually administered to patients in the form of a pharmaceutical composition which contains a non-toxic and effective amount of the compounds. The pharmaceutical composition is usually prepared by admixing the active compounds with conventional pharmaceutically acceptable carriers or diluents which are unreactive with the active compounds.

Suitable examples of the carrier and diluent are lactose, glucose, mannitol, dextrin, starch, sucrose, magnesium aluminometasilicate, synthetic aluminum silicate, crystalline cellulose, carboxymethylcellulose sodium, hydroxypropylstarch, carboxymethylcellulose calcium, ion exchange resin, methylcellulose, gelatin, gum arabic, hydroxypropylcellulose, low substituted hydroxypropylcellulose, hydroxypropylmethylcellulose, polyvinylpyrrolidone, polyvinyl alcohol, light anhydrous silicic acid, magnesium stearate, talc, carboxylvinyl polymer, titanium oxide, sorbitan fatty acid esters, sodium lauryl sulfate, glycerin, glycerin fatty acid esters, purified lanolin, glycerogelatin, polysorbate, macrogol, vegetable oils, wax, liquid paraffin, white petrolatum, nonionic surfactants, propylene glycol, and water.

The pharmaceutical composition may be in the dosage form of tablets, capsules, granules, powders, syrups, suspensions, suppositories, ointments, gels, adhesive preparations, injections, or ophthalmic solutions. These preparations can be prepared in a conventional manner. The liquid preparation may be in the form of a solid preparation convertible into liquid when used, that is, it is dissolved or suspended in water or any other appropriate vehicle when used. The tablets and granules may be coated with a conventional coating agent in a usual manner.

These pharmaceutical composition may contain the compound of the invention in an amount of 0.01% by weight or more, preferably 1 to 70% by weight, based upon the whole weight of the composition. These compositions may further contain one or more other pharmaceutically active ingredients such as oral hypoglycemic agent.

The pharmaceutical composition containing as an active ingredient the compound of the invention suitable for the prevention or treatment of diabetic complications may be used together with insulin or any other oral hypoglycemic agent such as gliclazide, glibenclamide, tolbutamide, acetohexamide, or glymidine sodium.

EXAMPLES

This invention is illustrated by the following Examples and Reference Examples, but should not be construed to be limited thereto. In these examples, the compounds were identified by elementary analysis, mass spectrum, IR spectrum, NMR spectrum, high performance liquid chromatography (HPLC) and the like.

EXAMPLE 1

Preparation of 2-(4-bromo-2-fluorobenzyl)-[1,2,3,4-tetrahydropyrrolo[1,2-a]pyrazine-4-spiro-3'-pyrrolidine]-1,2',3,5'-tetrone:

A mixture of 2-ethoxycarbonyl-2 (2-trichloroacetyl-pyrrol-1-yl)succinimide (14.8 g), 4-bromo-2-fluorobenzylamine hydrochloride (10.2 g) and triethylamine (9.0 g, 12.3 ml) in anhydrous dimethylformamide (150 ml) was stirred at 25° C. for 20 hours. The reaction mixture was poured into 5% hydrochloric acid and extracted with ethyl acetate. The extracts were dried over anhydrous sodium sulfate and concentrated under reduced pressure. The residue was chromatographed on silica gel using chloroform as the eluent. Fractions containing the title compound were pooled and evaporated under reduced pressure. The residue was recrystallized from ethyl acetate/n-hexane to give the title compound (6.5 g, 43.6%) as colorless crystals, mp 192°–193° C.

NMR spectrum (DMSO-$d_6$, 200 MHz): δ 3.56 (s, 2H, —CH$_2$CO—), 5.00 (dd, 2H, J=21.0 Hz, 15.0 Hz, —CH$_2$—Ar), 6.52 (dd, 1H, J=4.0 Hz, 2.8 Hz, pyrrole-H), 7.12 (dd, 1H, J=3.8 Hz, 1.4 Hz, pyrrole-H), 7.14 (t, 1H, J=8.2 Hz, Ar-H), 7.36 (dd, 1H, J=8.4 Hz, 2.0 Hz, Ar-H), 7.54 (dd, 1H, J=9.8 Hz, 2.0 Hz, Ar-H), 7.72 (dd, 1H, J=2.6 Hz, 1.6 Hz, pyrrole-H), 12.18 (s, 1H, NH).

IR spectrum (KBr, cm$^{-1}$): 3230, 3120, 1785, 1720, 1700, 1650, 1330, 1320.

EXAMPLE 2

Preparation of 2-(2-chlorobenzyl)-[1,2,3,4-tetrahydropyrrolo[1,2-a]pyrazine-4-spiro-3'-pyrrolidine]-1,2',3,5'-tetrone:

A mixture of 2-ethoxycarbonyl-2-(2-trichloroacetylpyrrol-1-yl)succinimide (2.4 g), 2-chlorobenzylamine (1.1 g) and triethylamine (1.3 g, 1.8 ml) in anhydrous dimethylformamide (15 ml) was stirred at 25° C. for 20 hours. The reaction mixture was poured into 5% hydrochloric acid and extracted with ethyl acetate. The extracts were dried over anhydrous sodium sulfate and concentrated under reduced pressure. The residue was chromatographed on silica gel using chloroform as the eluent. Fractions containing the title compound were pooled and evaporated under reduced pressure. The residue was recrystallized from ethyl acetate/n-hexane to give the title compound (0.96 g, 45.7%) as colorless crystals, mp 156°–158° C.

EXAMPLES 3 TO 18

The following compounds listed in Table 3 were prepared in substantially the same manner as described in Example 2, using the corresponding amine in place of 2-chlorobenzylamine in Example 2. After recrystallization from ethyl acetate/n-hexane, all compounds were obtained as colorless crystals.

TABLE 3

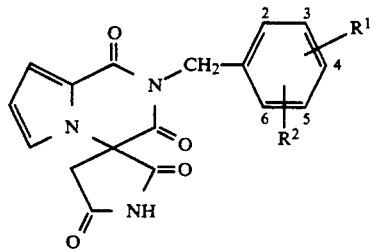

| Example | $R^1$ | $R^2$ | Melting Point (°C.) |
|---|---|---|---|
| 1 | H | H | 157–159 |
| 4 | 2-F | H | 166–168 |
| 5 | 3-Cl | H | 161–163 |
| 6 | 4-F | H | 189–190 |
| 7 | 4-Cl | H | 195–198 |
| 8 | 4-Br | H | 158–160 |
| 9 | 4-$CF_3$ | H | 182–183.5 |
| 10 | 2-F | 4-F | 221.5–223 |
| 11 | 4-$CH_3$ | H | 154–158 |
| 12 | 4-$OCH_3$ | H | 184–185 |
| 13 | 3-$OCH_3$ | 4-$OCH_3$ | 191–193 |
| 14 | 2-$OCH_3$ | 4-$OCH_3$ | 166–168 |
| 15 | 4-$NO_2$ | H | 211.5–213 (dec.) |
| 16 | 2-F | 4-Cl | 196–199 |
| 17 | 2-Br | H | 226–229 |
| 18 | 3-Br | H | 152–153 |

EXAMPLE 19

Preparation of 2-(4-bromo-2-fluorobenzyl)-7-chloro-[1,2,3,4-tetrahydropyrrolo[1,2-a]pyrazine-4-spiro-3'-pyrrolidine]-1,2',3,5'-tetrone:

A mixture of 2-(4-chloro-2-trichloroacetylpyrrol-1-yl)-2-ethoxycarbonylsuccinimide (2.1 g), 4-bromo-2-fluorobenzylamine hydrochloride (1.5 g) and triethylamine (1.9 g, 2.6 ml) in anhydrous dimethylformamide (30 ml) was stirred at 25° C. for 20 hours. The reaction mixture was treated in substantially the same manner as described in Example 2. The product was recrystallized from ethyl acetate/n-hexane to give the title compound (1.2 g, 52.2%) as colorless crystals, mp 227°–229° C.

EXAMPLE 20

Preparation of 7-bromo-2-(4-bromo-2-fluorobenzyl)-[1,2,3,4-tetrahydropyrrolo[1,2-a]pyrazine-4-spiro-3'-pyrrolidine]-1,2',3,5'-tetrone:

A mixture of 2-(4-bromo-2-trichloroacetylpyrrol-1-yl)-2-ethoxycarbonylsuccinimide (2.1 g), 4-bromo-2-fluorobenzylamine hydrochloride (1.3 g) and triethylamine (1.6 g, 2.2 ml) in anhydrous dimethylformamide (30 ml) was stirred at 25° C. for 20 hours. The reaction mixture was treated in substantially the same manner as described in Example 2. The product was recrystallized from ethyl acetate/n-hexane to give the title compound (1.2 g, 52.2%) as colorless crystals, mp 112°–114° C.

EXAMPLE 21

Preparation of 2-(4-bromo-2-fluorobenzyl)-[1,2,3,4-tetrahydropyrrolo[1,2-a]pyrazine-4-spiro-3'-pyrrolidine]-1,2',3,5'-tetrone (the same compound as that of Example 1):

A stirred solution of 2-(4-bromo-2-fluorobenzyl)-4-carbamoylmethyl-1,3-dioxo-1,2,3,4-tetrahydropyrrolo[1,2-a]pyrazine-4-carboxylic acid ethyl ester (1.9 g) in anhydrous dimethylformamide (15 ml) was cooled to −20° C., and then sodium hydride (63% dispersion in mineral oil, 0.29 g) was added portionwise. The resulting mixture was stirred at −20° C. for 15 minutes, poured into 5% hydrochloric acid, and extracted with ethyl acetate. The extracts were dried over anhydrous sodium sulfate and concentrated under reduced pressure. The residue was chromatographed on silica gel using chloroform/methanol (500:1) as the eluent. Fractions containing the title compound were pooled and evaporated under reduced pressure. The residue was recrystallized from ethyl acetate/n-hexane to give the title compound (0.6 g, 40.0%) as colorless crystals, mp 192°–193° C.

EXAMPLE 22

Preparation of an enantiomer of 2-(4-bromo-2-fluorobenzyl)-[1,2,3,4-tetrahydropyrrolo[1,2-a]pyrazine-4-spiro-3'-pyrrolidine]-1,2',3,5'-tetrone (Enantiomer A of compound of Example 1 or 21):

A stirred solution of 2-(4-bromo-2-fluorobenzyl)-4-carbamoylmethyl-1,3-dioxo-1,2,3,4-tetrahydropyrrolo[1,2-a]pyrazine-4-carboxylic acid (−)-menthyl ester (Diastereomer A) (26.7 g) in anhydrous tetrahydrofuran (120 ml) was cooled to −78° C., and then lithium bis(trimethylsilyl)amide (1M solution in tetrahydrofuran, 93 ml) was added dropwise over a 7 minute period, while a stream of argon was passed over the mixture. The resulting mixture was stirred at −78° C. for 5 minutes, poured into a cold aqueous ammonium chloride solution, acidified with dilute hydrochloric acid, and extracted with ethyl acetate. The extracts were washed with saturated aqueous sodium chloride solution, dried over anhydrous sodium sulfate, and concentrated under reduced pressure. The residue was chromatographed on silica gel using chloroform/methanol (200:1) as the eluent. Fractions containing the title compound were pooled and evaporated under reduced pressure. The residue was recrystallized from ethyl acetate/n-hexane to give the title compound (14.0 g, 72.2%) as colorless crystals, mp 187°–189° C.

The enantiomeric purity was determined by analytical HPLC, on ULTRON ES-OVM 6φ×150 mm (Shinwa kakoh, Japan) and was found to be greater than 99%.

$[\alpha]_D^{27.5} = +1.96°$ (C=1.02, ethyl acetate);
$[\alpha]_D^{28} = -7.6°$ (c=1.02, methanol);
$[\alpha]_{405}^{28} = -33.0°$ (c=1.02, methanol).

EXAMPLE 23

Preparation of an enantiomer of 2-(4-bromo-2-fluorobenzyl)-[1,2,3,4-tetrahydropyrrolo[1,2-a]pyrazine-4-spiro-3'-pyrrolidine]-1,2',3,5'-tetrone (Enantiomer B of compound of Example 1 or 21):

The procedure of Example 22 was repeated except that 2-(4-bromo-2-fluorobenzyl)-4-carbamoylmethyl-1,3-dioxo-1,2,3,4-tetrahydropyrrolo[1,2-a]pyrazine-4-carboxylic acid (−)-menthyl ester (Diastereomer B) (22.2 g) was used in place of the corresponding Diastereomer A. The title compound (11.3 g, 69.7%) was obtained as colorless crystals, mp 187°–189° C. (recrystallized from ethyl acetate/n-hexane).

The enantiomeric purity was determined by analytical HPLC, On ULTRON ES-OVM column 6$\phi$×150 mm and was found to be greater than 99%.

$[\alpha]_D^{27.5} = -1.67°$ (c=1.02, ethyl acetate);
$[\alpha]_D^{28} = +6.1°$ (c=1.02, methanol);
$[\alpha]_{405}^{28} = +33.2°$ (c=1.02, methanol).

EXAMPLE 24

Preparation of 2-(3,4-dichlorobenzyl)-[1,2,3,4-tetrahydropyrrolo[1,2-a]pyrazine-4-spiro-3'-pyrrolidine]-1,2',3,5'-tetrone:

The procedure of Example 21 was repeated except that 4-carbamoylmethyl-2-(3,4-dichlorobenzyl)-1,3-dioxo-1,2,3,4-tetrahydropyrrolo[1,2-a]pyrazine-4-carboxylic acid benzyl ester was used in place of 2-(4-bromo-2-fluorobenzyl)-4-carbamoylmethyl-1,3-dioxo-1,2,3,4-tetrahydropyrrolo[1,2-a]pyrazine-4-carboxylic acid ethyl ester. The title compound was obtained as colorless crystals, mp 221°–223° C. (recrystallized from ethyl acetate/n-hexane).

EXAMPLE 25

Preparation of 6-bromo-2-(2-chlorobenzyl)-[1,2,3,4-tetrahydropyrrolo[1,2-a]pyrazine-4-spiro-3'-pyrrolidine]-1,2',3,5'-tetrone:

To a stirred solution of 2-(2-chlorobenzyl)-[1,2,3,4-tetrahydropyrrolo[1,2-a]pyrazine-4-spiro-3'-pyrrolidine]-1,2',3,5'-tetrone (0.5 g) in chloroform (80 ml) was added portionwise anhydrous aluminum chloride (0.93 g) at 25° C., followed by dropwise addition of a solution of bromine (0.48 g) in chloroform (4 ml). The resulting mixture was stirred at 25° C. for 15 hours, poured into ice-water, and extracted with chloroform. The extracts were dried over sodium sulfate and concentrated under reduced pressure. The residue was applied to a medium pressure column chromatography on Diaion CHP-20P (trademark) [high porous polymer (75–150 μm); Mitsubishi Kasei Corp., Japan], using 61% acetonitrile as the eluent. Fractions containing the title compound were pooled and evaporated under reduced pressure. The residue was recrystallized from ethyl acetate/n-hexane to give the title compound (0.37 g, 60.7%) as colorless crystals, mp 201°–203° C.

EXAMPLE 26

Preparation of 6-bromo-2-(4-bromo-2-fluorobenzyl)-[1,2,3,4-tetrahydropyrrolo[1,2-a]pyrazine-4-spiro-3'-pyrrolidine]-1,2',3,5'-tetrone:

To a stirred solution of 2-(4-bromo-2-fluorobenzyl)-[1,2,3,4-tetrahydropyrrolo[1,2-a]pyrazine-4-spiro-3'-pyrrolidine]-1,2',3,5'-tetrone (0.9 g) in chloroform (350 ml) was added portionwise anhydrous aluminum chloride (1.4 g) at 25° C., followed by dropwise addition of a solution of bromine (0.68 g) in chloroform (7 ml). The resulting mixture was stirred at 50° C. for 15 hours, poured into ice-water, and extracted with chloroform. The extracts were dried over sodium sulfate and concentrated under reduced pressure. The residue was applied to a medium pressure column chromatography on Diaion CHP-20P using 61% acetonitrile as the eluent. Fractions containing the title compound were pooled and evaporated under reduced pressure. The residue was recrystallized from ethyl acetate/n-hexane to give the title compound (0.34 g, 30.9%) as colorless crystals, mp 209°–211° C. (decomp.).

EXAMPLE 27

Preparation of 2-(4 bromo-2-fluorobenzyl)-6-chloro-[1,2,3,4-tetrahydropyrrolo[1,2-a]pyrazine-4-spiro-3'-pyrrolidine]-1,2',3,5 -tetrone:

To a stirred solution of 2-(4-bromo-2-fluorobenzyl)-[1,2,3,4-tetrahydropyrrolo[1,2-a]pyrazine-4-spiro-3'-pyrrolidine]-1,2',3,5'-tetrone (0.9 g) in chloroform (350 ml) was added portionwise sulfuryl chloride (0.68 g) at 25° C. The resulting mixture was stirred at 25° C. for 4 hours, poured into ice-water, and extracted with chloroform. The extracts were dried over sodium sulfate and concentrated under reduced pressure. The residue was applied to a medium pressure column chromatography on Diaion CHP-20P using 50% acetonitrile as the eluent. Fractions containing the title compound were pooled and evaporated under reduced pressure. The residue was recrystallized from ethyl acetate/n-hexane to give the title compound (0.56 g, 50.9%) as colorless crystals, mp 207°–209° C.

The starting materials used in the foregoing Examples were prepared as follows.

REFERENCE EXAMPLE 1

Preparation of 2-(pyrrol-1-yl)malonic acid dibenzyl ester:

To a solution of 2-(pyrrol-1-yl)malonic acid diethyl ester (75.7 g) in benzyl alcohol (200 ml) was added tetraethyl titanate (3.0 g), and the resulting mixture was stirred at 110° C. for 15 hours. After removal of the benzyl alcohol under reduced pressure, the residue was chromatographed on silica gel using n-hexane/ethyl acetate (10:1) as the eluent. Fractions containing the title compound were pooled and evaporated under reduced pressure. The residue was recrystallized from ethyl acetate/n-hexane to give the title compound (102.5 g, 87.3%) as colorless crystals, mp 48.5°–49° C.

REFERENCE EXAMPLE 2

Preparation of 2-(pyrrol-1-yl)malonic acid ethyl (−)-menthyl ester:

To a mixture of 2-(pyrrol-1-yl)malonic acid diethyl ester (300.0 g) and (−)-menthol (417.0 g) was added tetraethyl titanate (10.0 g), and the resulting mixture was stirred at 110° C. for 19 hours. After removal of the (−)-menthol under reduced pressure, the residue was chromatographed on silica gel using n-hexane/ethyl acetate (50:1) as the eluent. Fractions containing the title compound were pooled and evaporated under reduced pressure to give the title compound (142.0 g, 31.8%) as a colorless oil.

REFERENCE EXAMPLE 3

Preparation of 2-benzyloxycarbonylmethyl-2-(pyrrol-1-yl)malonic acid diethyl ester:

To a stirred solution of 2-(pyrrol-1-yl)malonic acid diethyl ester (53.0 g) in anhydrous dimethylformamide (300 ml) was added portionwise sodium hydride (63% dispersion in mineral oil, 10.0 g) under ice cooling. The resulting mixture was stirred at 25° C. for 30 minutes and thereto was added benzyl bromoacetate (70.1 g). After stirring at 25° C. for 15 hours, the reaction mixture was poured into water and extracted with ethyl acetate. The extracts were dried over anhydrous sodium sulfate and concentrated under reduced pressure. The residue was chromatographed on silica gel using n-hexane/ethyl acetate (10:1) as the eluent. Fractions containing the title compound were pooled and evaporated under reduced pressure to give the title compound (80.0 g, 91.0%) as a colorless oil.

REFERENCE EXAMPLE 4

Preparation of 2-carboxymethyl-2-(pyrrol-1-yl)-malonic acid diethyl ester:

A mixture of 2-benzyloxycarbonylmethyl-2-(pyrrol-1-yl)malonic acid diethyl ester (80.0 g) in dioxane (150 ml) was hydrogenated over 10% palladium-carbon (500 mg) at 40° C. After the calculated amount of hydrogen was absorbed, the catalyst was filtered off and the filtrate was evaporated under reduced pressure. The residue was recrystallized from ethyl acetate/n-hexane to give the title compound (48.7 g, 80.2%) as colorless crystals, mp 93°-94° C.

REFERENCE EXAMPLE 5

Preparation of 2-carbamoylmethyl-2-(pyrrol-1-yl)-malonic acid diethyl ester:

A mixture of 2-carboxymethyl-2-(pyrrol-1-yl)-malonic acid diethyl ester (36.0 g), N-hydroxysuccinimide (16.1 g) and 1-ethyl-3-(3-dimethylaminopropyl)-carbodiimide hydrochloride (29.2 g) in dichloromethane (200 ml) was stirred at 25° C. for 1 hour, followed by addition of 7.8% (w/w) ammonia in acetonitrile (110 ml). The resulting mixture was stirred at 25° C. for 1 hour and concentrated under reduced pressure at the same temperature. The residue was dissolved in ethyl acetate. The solution was washed with 5% hydrochloric acid and then with saturated aqueous sodium chloride solution, dried over anhydrous sodium sulfate, and evaporated under reduced pressure. The residue was recrystallized from ethyl acetate/n-hexane to give the title compound (29.0 g, 80.8%) as colorless crystals, mp 94°-95° C.

REFERENCE EXAMPLE 6

Preparation of 2-ethoxycarbonyl-2-(pyrrol-1-yl)-succinimide:

To a stirred solution of 2-carbamoylmethyl-2-(pyrrol-1-yl)malonic acid diethyl ester (29.0 g) in anhydrous dimethylformamide (30 ml) was added portionwise sodium hydride (63% dispersion in mineral oil, 4.3 g) under ice cooling. The resulting mixture was stirred under ice cooling for 1 hour, poured into 5% hydrochloric acid/ice-water, and extracted with ethyl acetate. The extracts were washed with saturated aqueous sodium chloride solution, dried over anhydrous sodium sulfate, and concentrated under reduced pressure. The residue was chromatographed on silica gel using n-hexane/ethyl acetate (2:1) as the eluent. Fractions containing the title compound were pooled and evaporated under reduced pressure to give the title compound (23.0 g, 94.7%) as a colorless oil.

REFERENCE EXAMPLE 7

Preparation of 2-ethoxycarbonyl-2-(2-trichloroacetylpyrrol-1-yl)succinimide.¼ dimethylformamide:

To a solution of 2-ethoxycarbonyl-2-(pyrrol-1-yl)-succinimide (18.0 g) in chloroform (40 ml) was added trichloroacetyl chloride (42.0 g), and the resulting mixture was refluxed for 67 hours. The reaction mixture was concentrated under reduced pressure, and the residue was dissolved in ethyl acetate. The solution was washed with 10% aqueous sodium carbonate solution and then with saturated aqueous sodium chloride solution, dried over anhydrous sodium sulfate, and concentrated under reduced pressure. The residue was chromatographed on silica gel using n-hexane/ethyl acetate (4:1) as the eluent. Fractions containing the title compound were pooled and evaporated under reduced pressure. The crude product obtained as a colorless oil was treated with dimethylformamide (5 ml) to crystallize. Recrystallization from ethyl acetate/n-hexane gave the title compound (28.5 g, 89.3%) as colorless crystals, mp 94°-97° C.

REFERENCE EXAMPLE 8

Preparation of 2-(2-trichloroacetylpyrrol-1-yl)malonic acid diethyl ester:

To a solution of 2-(pyrrol-1-yl)malonic acid diethyl ester (100.0 g) in chloroform (100 ml) was added trichloroacetyl chloride (161.4 g), and the resulting mixture was refluxed for 15 hours. The reaction mixture was concentrated under reduced pressure, and the residue was dissolved in ethyl acetate. The solution was washed with 10% aqueous sodium carbonate solution and then with saturated aqueous sodium chloride solution, dried over anhydrous sodium sulfate, and evaporated under reduced pressure. The residue was recrystallized from isopropyl ether to give the title compound (146.4 g, 89.0%) as colorless crystals, mp 67°-69° C.

REFERENCE EXAMPLE 9

Preparation of 2-(2-trichloroacetylpyrrol-1-yl)malonic acid ethyl (−)-menthyl ester:

To a solution of 2-(pyrrol-1-yl)malonic acid ethyl (−)-menthyl ester (64.0 g) in chloroform (80 ml) was added trichloroacetyl chloride (69.0 g), and the resulting mixture was refluxed for 7 hours. The reaction mixture was concentrated under reduced pressure, and the residue was dissolved in ethyl acetate. The solution was washed with 5% aqueous sodium carbonate solution and then with saturated aqueous sodium chloride solution, dried over anhydrous sodium sulfate, and concentrated under reduced pressure. The residue was chromatographed on silica gel using n-hexane/ethyl acetate (50:1) as the eluent. Fractions containing the title compound were pooled and evaporated under reduced pressure to give the title compound (87.0 g, 94.9%) as a colorless oil.

REFERENCE EXAMPLE 10

Preparation of 2-(trichloroacetylpyrrol-1-yl)malonic acid dibenzyl ester:

The procedure of Reference Example 8 was repeated except that 2-(pyrrol-1-yl)malonic acid dibenzyl ester was used in place of 2-(pyrrol-1-yl)malonic acid diethyl ester. The title compound was obtained as colorless crystals, mp 74°-76° C. (recrystallized from ethyl acetate/n-hexane).

REFERENCE EXAMPLE 11

Preparation of 2-(4-bromo-2-fluorobenzyl)-1,3-dioxo-1,2,3,4-tetrahydropyrrolo[1,2-a]pyrazine-4-carboxylic acid ethyl ester:

A mixture of 2-(2-trichloroacetylpyrrol-1-yl)malonic acid diethyl ester (40.0 g), 4-bromo-2-fluorobenzylamine hydrochloride (29.0 g) and triethylamine (54.8 g, 75.0 ml) in anhydrous dimethylformamide (100 ml) was stirred under the stream of nitrogen at 70° C. for 1 hour. After cooling, the reaction mixture was poured into 5% hydrochloric acid and extracted with ethyl acetate. The extracts were dried over anhydrous sodium sulfate and evaporated under reduced pressure. The residue was recrystallized from ethyl acetate/n-hexane to give the title compound (38.0 g, 86.0%) as colorless crystals, mp 114°-115° C.

REFERENCE EXAMPLE 12

Preparation of 2-(4-bromo-2-fluorobenzyl)-1,3-dioxo-1,2,3,4-tetrahydropyrrolo[1,2-a]pyrazine-4-carboxylic acid (−)-menthyl ester:

A mixture of 2-(2-trichloroacetylpyrrol-1-yl)malonic acid ethyl (−)-menthyl ester (87.0 g), 4-bromo-2-fluorobenzylamine hydrochloride (53.0 g) and triethylamine (66.4 g, 91.0 ml) in anhydrous dimethylformamide (200 ml) was stirred under the stream of nitrogen at 75° C. for 2 hours. The reaction mixture was concentrated under reduced pressure and the residue was dissolved in ethyl acetate. The solution was washed with 5% cold hydrochloric acid and then with saturated aqueous sodium chloride solution, dried over anhydrous sodium sulfate, and evaporated under reduced pressure. The residue was recrystallized from methanol to give the title compound (74.0 g, 78.7%) as colorless crystals, mp 98°-99° C.

REFERENCE EXAMPLE 13

Preparation of 2-(3,4-dichlorobenzyl)-1,3-dioxo-1,2,3,4-tetrahydropyrrolo[1,2-a]pyrazine-4-carboxylic acid benzyl ester:

A mixture of 2-(2-trichloroacetylpyrrol-1-yl)malonic acid dibenzyl ester (30.0 g), 3,4 dichlorobenzylamine (11.7 g) and triethylamine (18.4 g, 25.0 ml) in anhydrous dimethylformamide (70 ml) was stirred under the stream of nitrogen at 70° C. for 2 hours. After cooling, the reaction mixture was poured into 5% hydrochloric acid and extracted with ethyl acetate. The extracts were dried over anhydrous sodium sulfate and concentrated under reduced pressure. The residue was chromatographed on silica gel using n-hexane/ethyl acetate (3:1) as the eluent. Fractions containing the title compound were pooled and evaporated under reduced pressure. The residue was recrystallized from ethyl acetate/n-hexane to give the title compound (16.0 g, 59.5%) as colorless crystals, mp 104°-106° C.

REFERENCE EXAMPLE 14

Preparation of 4-benzyloxycarbonyl-2-(3,4-dichlorobenzyl)-1,3-dioxo-1,2,3,4-tetrahydropyrrolo[1,2-a]pyrazine-4-acetic acid tert-butyl ester:

To a stirred solution of 2-(3,4-dichlorobenzyl)-1,3-dioxo-1,2,3,4-tetrahydropyrrolo[1,2-a]pyrazine-4-carboxylic acid benzyl ester (9.4 g) in anhydrous dimethylformamide (40 ml) was added portionwise sodium hydride (63% dispersion in mineral oil, 0.7 g) under ice cooling, while a stream of nitrogen was passed over the mixture. The resulting mixture was stirred at 25° C. for 1 hour and thereto was added tert-butyl bromoacetate (4.3 g). The mixture was stirred at 25° C. for 15 hours, poured into water, and extracted with ethyl acetate. The extracts were dried over anhydrous sodium sulfate and concentrated under reduced pressure. The residue was chromatographed on silica gel using n-hexane/ethyl acetate (20:1) as the eluent. Fractions containing the title compound were pooled and evaporated under reduced pressure. The residue was recrystallized from ethyl acetate/n-hexane to give the title compound (9.2 g, 78.0%) as colorless crystals, mp 86°-88° C.

REFERENCE EXAMPLE 15

Preparation of 2-(4-bromo-2-fluorobenzyl)-4-ethoxycarbonyl-1,3-dioxo-1,2,3,4-tetrahydropyrrolo[1,2-a]pyrazine-4-acetic acid tert-butyl ester:

A mixture of 2-(2-trichloroacetylpyrrol-1-yl)malonic acid diethyl ester (25.0 g), 4-bromo-2-fluorobenzylamine hydrochloride (17.8 g) and triethylamine (22.5 g, 30.8 ml) in anhydrous dimethylformamide (100 ml) was stirred under the stream of nitrogen at 70° C. for 1 hour and concentrated under reduced pressure. The residue was dissolved in anhydrous dimethylformamide (100 ml) and to the stirred solution under the stream of nitrogen was added portionwise sodium hydride (63% dispersion in mineral oil, 5.6 g) under ice cooling. The resulting mixture was stirred at 25° C. for 1 hour and thereto was added tert-butyl bromoacetate (31.6 g). The mixture was stirred at 25° C. for 15 hours, poured into water, and extracted with ethyl acetate. The extracts were dried over anhydrous sodium sulfate and concentrated under reduced pressure. The residue was chromatographed on silica gel using n-hexane/ethyl acetate (8:1) as the eluent. Fractions containing the title compound were pooled and evaporated under reduced pressure to give the title compound (28.7 g, 81.3%) as a colorless oil.

REFERENCE EXAMPLE 16

Preparation of a diastereomer of 2-(4-bromo-2-fluorobenzyl)-4-(−)-menthyloxycarbonyl-1,3-dioxo-1,2,3,4-tetrahydropyrrolo[1,2-a]pyrazine-4-acetic acid tert-butyl ester (Diastereomer A and Diastereomer B):

(1) A mixture of 2-(4-bromo-2-fluorobenzyl)-1,3-dioxo-1,2,3,4-tetrahydropyrrolo[1,2-a]pyrazine-4-carboxylic acid (−)-menthyl ester (67.0 g), anhydrous potassium carbonate (36.0 g) and tert-butyl bromoacetate (33.0 g) in anhydrous dimethylformamide (200 ml) was stirred under the stream of nitrogen at 70° C. for 2.5 hours. After removal of the insoluble materials by filtration, the filtrate was poured into water and extracted with ethyl acetate. The extracts were washed with saturated aqueous sodium chloride solution, dried over anhydrous sodium sulfate, and evaporated under reduced pressure. The residue was recrystallized from n-hexane to give the title compound (Diastereomer A) (23.5 g, 28.8%) as colorless crystals, mp 99°-100° C.

The diastereomeric purity was determined by analytical HPLC, on CAPCELL PAK C18 4.6$\phi$×150 mm (Shiseido Co., Ltd., Japan) and was found to be greater than 99%. $[\alpha]_D^{26} = -24.8°$ (c=1.01, ethanol)

(2) The mother liquor obtained after separation of the above Diastereomer A was evaporated under reduced pressure. The residue was purified by chromatography on silica gel, using n hexane/dichloromethane (1:1) as the eluent, to give the title compound (Diastereomer B) (26.7 g, 32.7%) as a colorless oil.

The diastereomeric purity was determined by the same method as above and was found to be greater than 99%.

REFERENCE EXAMPLE 17

Preparation of 2-(4-bromo-2-fluorobenzyl)-4-ethoxycarbonyl-1,3-dioxo-1,2,3,4-tetrahydropyrrolo[1,2-a]pyrazine-4-acetic acid:

A mixture of 2-(4-bromo-2-fluorobenzyl)-4-ethoxycarbonyl-1,3-dioxo-1,2,3,4-tetrahydropyrrolo[1,2-a]pyrazine-4-acetic acid tert-butyl ester (28.7 g) and trifluoroacetic acid (125.1 g, 84.5 ml) in dichloromethane (100 ml) was refluxed for 3 hours and concentrated under reduced pressure. The residue was chromatographed on silica gel using chloroform as the eluent. Fractions containing the title compound were pooled and evaporated under reduced pressure. The residue was recrystallized from ethyl acetate/n-hexane to give the title compound (21.4 g, 3.6%) as colorless crystals, mp 142°-144° C.

REFERENCE EXAMPLE 18

Preparation of a diastereomer of 2-(4-bromo-2-fluorobenzyl)-4-(−)-menthyloxycarbonyl-1,3-dioxo-1,2,3,4-tetrahydropyrrolo[1,2-a]pyrazine-4-acetic acid (Diastereomer A and Diastereomer B):

(1) A mixture of 2-(4-bromo-2-fluorobenzyl)-4-(−)-menthyloxycarbonyl-1,3-dioxo-1,2,3,4-tetrahydropyrrolo[1,2-a]pyrazine-4-acetic acid tert-butyl ester (Diastereomer A) (30.0 g) and trifluoroacetic acid (112.5 g, 76.0 ml) in anhydrous dichloromethane (120 ml) was refluxed for 1.5 hours and concentrated under reduced pressure. The residue was dissolved in a mixture of acetonitrile and toluene. The resulting solution was evaporated under reduced pressure to give the title compound (Diastereomer A) (27.3 g, quantitative) as a brown oil.

(2) Repeating the above procedure, using 2-(4-bromo-2-fluorobenzyl)-4-(−)-menthyloxycarbonyl-1,3-dioxo-1,2,3,4-tetrahydropyrrolo[1,2-a]pyrazine-4-acetic acid tert-butyl ester (Diastereomer B) (26.7 g) in place of the corresponding Diastereomer A, gave the title compound (Diastereomer B) (23.7 g, quantitative).

REFERENCE EXAMPLE 19

Preparation of 2-(4-bromo 2-fluorobenzyl)-4-carbamoylmethyl-1,3-dioxo-1,2,3,4-tetrahydropyrrolo[1,2-a]pyrazine-4-carboxylic acid ethyl ester:

A mixture of 2-(4-bromo-2-fluorobenzyl)-4-ethoxycarbonyl-1,3-dioxo-1,2,3,4-tetrahydropyrrolo[1,2-a]pyrazine-4-acetic acid (21.4 g), N-hydroxysuccinimide (5.8 g) and 1-ethyl-3-(3-dimethylaminopropyl)carbodiimide hydrochloride (10.5 g) in dichloromethane (150 ml) was stirred at 25° C. for 1 hour, and 7.8% (w/w) ammonia in acetonitrile (40 ml) was added. The resulting mixture was stirred at 25° C. for 1 hour, poured into 5% hydrochloric acid, and extracted with dichloromethane. The extracts were dried over anhydrous sodium sulfate and evaporated under reduced pressure. The residue was recrystallized from ethyl acetate/n-hexane to give the title compound (18.5 g, 86.4%) as colorless crystals, mp 190°-192° C.

REFERENCE EXAMPLE 20

Preparation of a diastereomer of 2-(4-bromo-2-fluorobenzyl)-4-carbamoylmethyl-1,3-dioxo-1,2,3,4-tetrahydropyrrolo[1,2-a]pyrazine-4-carboxylic acid (−)-menthyl ester (Diastereomer A and Diastereomer B):

(1) To a solution of 2-(4-bromo-2-fluorobenzyl)-4-(−)-menthyloxycarbonyl-1,3-dioxo-1,2,3,4-tetrahydropyrrolo[1,2-a]pyrazine-4-acetic acid (Diastereomer A) (27.3 g) in anhydrous dichloromethane (80 ml) was added thionyl chloride (14 ml). The resulting solution was refluxed for 2 hours and concentrated under reduced pressure. The residue was dissolved in dichloromethane (80 ml) and the solution was concentrated under reduced pressure. To a solution of the residue in dichloromethane (100 ml) was added 7% (w/w) ammonia in acetonitrile (50 ml) under ice cooling. The resulting mixture was stirred at 25° C. for 30 minutes and concentrated under reduced pressure. The residue was dissolved in ethyl acetate. The solution was washed with water, dried over anhydrous sodium sulfate, and evaporated under reduced pressure. The residue was recrystallized from ethyl acetate/n-hexane to give the title compound (Diastereomer A) (26.7 g, 97.8%) as colorless crystals, mp 207°-209° C.

(2) Repeating the above procedure, using 2-(4-bromo-2-fluorobenzyl)-4-(−)-menthyloxycarbonyl-1,3-dioxo-1,2,3,4-tetrahydropyrrolo[1,2-a]pyrazine-4-acetic acid (Diastereomer B) (23.7 g) in place of the corresponding Diastereomer A, gave the title compound (Diastereomer B) (22.2 g, 93.7%), mp 122°-123° C. (recrystallized from ethyl acetate/n-hexane).

REFERENCE EXAMPLE 21

Preparation of 4-carbamoylmethyl-2-(3,4-dichlorobenzyl)-1,3-dioxo-1,2,3,4-tetrahydropyrrolo[1,2-a]pyrazine-4-carboxylic acid benzyl ester:

The procedure of Reference Example 17 was repeated except that 4-benzyloxycarbonyl-2-(3,4-dichlorobenzyl)-1,3-dioxo-1,2,3,4-tetrahydropyrrolo[1,2-a]pyrazine-4-acetic acid tert-butyl ester was used in place of 2-(4-bromo-2-fluorobenzyl)-4-ethoxycarbonyl-1,3-dioxo-1,2,3,4-tetrahydropyrrolo[1,2-a]pyrazine-4-acetic acid tert-butyl ester. There was obtained 4-benzyloxycarbonyl-2-(3,4-dichlorobenzyl)-1,3-dioxo-1,2,3,4tetrahydropyrrolo[1,2-a]pyrazine-4-acetic acid. The product was treated in substantially the same manner as described in Reference Example 19 to give the title compound, mp 134°-136° C. (recrystallized from ethyl acetate/n-hexane).

REFERENCE EXAMPLE 22

Preparation of 2-(4-chloro-2-trichloroacetylpyrrol-1-yl)-2-ethoxycarbonylsuccinimide:

To a stirred solution of 2-ethoxycarbonyl-2-(2-trichloroacetylpyrrol-1-yl)succinimide (6.0 g) in chloroform (50 ml) was added dropwise a solution of sulfuryl chloride (4.8 g) in chloroform (5 ml) under ice cooling. The resulting mixture was stirred under ice cooling for 30 minutes, poured into water, and extracted with chloroform. The extracts were dried over sodium sulfate and concentrated under reduced pressure. The residue was chromatographed on silica gel using n-hexane/ethyl acetate (2:1) as the eluent. Fractions containing the title compound were pooled and evaporated under reduced pressure. The residue was recrystallized from ethyl acetate/n-hexane to give the title compound (2.5 g, 41.7%) as colorless crystals, mp 182°-185° C.

REFERENCE EXAMPLE 23

Preparation of 2-(4-bromo-2-trichloroacetylpyrrol-1-yl)-2-ethoxycarbonylsuccinimide:

To a stirred solution of 2-ethoxycarbonyl-2-(2-trichloroacetylpyrrol-1-yl)succinimide (6.0 g) in chloroform (30 ml) was added dropwise a solution of bromine (6.9 g) in chloroform (18 ml) under ice cooling. The resulting mixture was stirred under ice cooling for 30 minutes, poured into aqueous sodium bicarbonate solution, and extracted with chloroform. The extracts were dried over sodium sulfate and concentrated under reduced pressure. The residue was chromatographed on silica gel using chloroform/methanol (2000:1) as the eluent. Fractions containing the title compound were pooled and evaporated under reduced pressure. The residue was recrystallized from ethyl acetate/n-hexane to give the title compound (2.4 g, 36.4%) as colorless crystals, mp 196°–198° C.

REFERENCE EXAMPLE 24

Preparation of 2-benzyloxycarbonylamino-2-cyanoacetic acid ethyl ester:

To a stirred mixture of 2-amino-2-cyanoacetic acid ethyl ester (19.7 g) and pyridine (12.2 g) in water (123 ml) was added portionwise benzyloxycarbonyl chloride (27.9 g) under ice cooling. The resulting mixture was stirred under ice cooling for 1 hour. Precipitated crystals were collected, washed thoroughly with water, and recrystallized from ethanol to give the title compound (24.2 g, 60.2%) as colorless crystals, mp 111°–112° C.

REFERENCE EXAMPLE 25

Preparation of 2-benzyloxycarbonylamino-2-cyanosuccinic acid diethyl ester:

To a sodium ethoxide solution, which was prepared from sodium (2.11 g) and ethanol (400 ml), were added in turn 2-benzyloxycarbonylamino-2-cyanoacetic acid ethyl ester (24.0 g) and ethyl bromoacetate (15.3 g). The resulting mixture was stirred at 25° C. for 3 hours and concentrated under reduced pressure. The residue was diluted with water and extracted with chloroform. The extracts were washed with water, dried over anhydrous sodium sulfate, and evaporated under reduced pressure to give the title compound (31.6 g, 99%) as a colorless oil.

REFERENCE EXAMPLE 26

Preparation of 2-benzyloxycarbonylamino-2-ethoxycarbonylsuccinimide:

A solution of 2-benzyloxycarbonylamino-2-cyanosuccinic acid diethyl ester (15.4 g) in dichloromethane (50 ml) was cooled to ice-bath temperature, and then 30% hydrogen peroxide (21 ml), tetrabutylammonium hydrogen sulfate (3.0 g) and 20% aqueous sodium hydroxide solution (16.6 ml) were added in turn. The resulting mixture was stirred under ice cooling for 30 minutes and then at 25° C. for 1 hour. The organic layer was separated, washed with water, dried over anhydrous sodium sulfate, and concentrated under reduced pressure. The residue was heated at 80° C. for 1.5 hours to give the title compound (11.5 g, 81.2%), which was recrystallized from ethyl acetate/n-hexane to give the pure product, mp 105°–106° C.

REFERENCE EXAMPLE 27

Preparation of 2-amino-2-ethoxycarbonylsuccinimde:

A solution of 2 benzyloxycarbonylamino-2-ethoxycarbonylsuccinimide (60.0 g) in acetic acid (350 ml) was hydrogenated over 10% palladium-carbon (6 g) at 25° C. After the calculated amount of hydrogen was absorbed, the catalyst was filtered off and the filtrate was concentrated under reduced pressure. The residue was diluted with water, adjusted to the pH of about 7 with saturated aqueous sodium bicarbonate solution, and extracted with ethyl acetate. The extracts were dried over anhydrous sodium sulfate and evaporated under reduced pressure. The residue was recrystallized from ethanol to give the title compound (12.8 g, 37%) as colorless crystals, mp 107°–108° C.

REFERENCE EXAMPLE 28

Preparation of 2-ethoxycarbonyl-2-(pyrrol-1-yl)succinimide (the same compound as that of Reference Example 6):

To a solution of 2-amino-2-ethoxycarbonylsuccinimide (7.0 g) in acetic acid (35 ml) was added 2,5-dimethoxytetrahydrofuran (5.0 g). The resulting mixture was refluxed for 50 minutes and concentrated under reduced pressure. The residue was diluted with ethyl acetate, washed with aqueous sodium bicarbonate solution and then with water, and dried over anhydrous sodium sulfate. After removal of the solvent under reduced pressure, the residue was chromatographed on silica gel using n-hexane/ethyl acetate (2:1) as the eluent. Fractions containing the title compound were pooled and evaporated under reduced pressure to give the title compound (8.0 g, 90%) as a colorless oil.

EXAMPLE 28

| per 1,000 tablets | |
|---|---|
| Enantiomer A of 2-(4-bromo-2-fluorobenzyl)-[1,2,3,4-tetra-hydropyrrolo[1,2-a]pyrazine-4-spiro-3'-pyrrolidine]-1,2',3,5'-tetrone (compound of Example 22) | 1 g |
| Corn starch | 25 g |
| Lactose | 58 g |
| Crystalline cellulose | 11 g |
| Hydroxypropylcellulose | 3 g |
| Light anhydrous silicic acid | 1 g |
| Magnesium stearate | 1 g |

The above components are blended, granulated and made into 1,000 tablets each weighing 100 mg by a conventional method.

EXAMPLE 29

| fine granules | |
|---|---|
| 2-(4-Bromo-2-fluorobenzyl)-[1,2,3,4-tetrahydropyrrolo[1,2-a]pyrazine-4-spiro-3'-pyrrolidine]-1,2',3,5'-tetrone (compound of Example 1 or 21) | 10 g |
| Corn starch | 220 g |
| Lactose | 730 g |
| Hydroxypropylcellulose | 30 g |
| Light anhydrous silicic acid | 10 g |

The above components are blended and made into fine granules by a conventional method.

What is claimed is:

1. A compound of the formula:

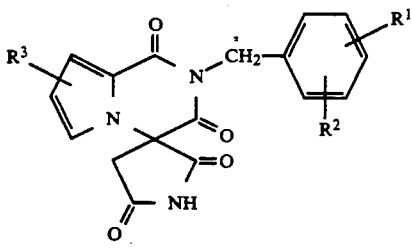

wherein $R^1$ and $R^2$ are independently hydrogen, halogen, trifluoromethyl, alkyl having 1 to 6 carbon atoms, alkoxy having 1 to 6 carbon atoms, or nitro, and $R^3$ is hydrogen, halogen or alkyl having 1 to 6 carbon atoms, or a pharmaceutically acceptable salt thereof.

2. A compound according to claim 1, wherein $R^3$ is hydrogen or halogen, or methyl at the 7-position, or a pharmaceutically acceptable salt thereof.

3. A compound according to claim 2, wherein $R^1$ and $R^2$ are independently hydrogen or halogen, or a pharmaceutically acceptable salt thereof.

4. A compound according to claim 2, wherein $R^1$ is alkyl having 1 to 3 carbon atoms or alkoxy having 1 to 3 carbon atoms, and $R^2$ is hydrogen, or a pharmaceutically acceptable salt thereof.

5. A compound according to claim 1, wherein $R^1$ is hydrogen or halogen, $R^2$ is halogen and $R^3$ is hydrogen.

6. A compound according to claim 5, which is the enantiomeric form having more potent aldose reductase inhibitory activity compared with the other enantiomer.

7. A compound according to claim 5, which is in the form of racemic compound.

8. A compound which is represented by the following formula:

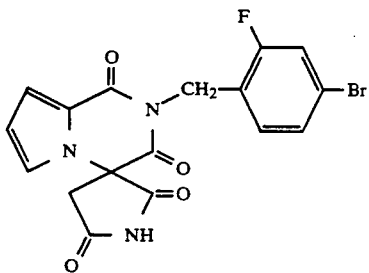

9. The compound according to claim 8, which is in the form of an enantiomer having the following specific rotation: $[\alpha]_D^{27.5} = +1.96°$ (c=1.02, ethyl acetate); $[\alpha]_D^{28} = -7.6°$ (c=1.02, methanol); and $[\alpha]_{405}^{28} = -33.0°$ (c=1.02, methanol).

10. The compound according to claim 8, which is the racemate 2-(4-bromo-2-fluorobenzyl)-[1,2,3,4-tetrahydropyrrolo[1,2-a]-pyrazine-4-spiro-3'-pyrrolidine]-1,2',3,5'-tetrone.

11. A compound according to claim, 5, which is selected from the group consisting of
2-(3,4 dichlorobenzyl)-[1,2,3,4-tetrahydropyrrolo-1,2-a]pyrazine-4-spiro-3'-pyrrolidine]-1,2',3,5'-tetrone,
2-(4-bromobenzyl)-[1,2,3,4-tetrahydropyrrolo[1,2-a]pyrazine-4-spiro-3'-pyrrolidine]-1,2',3,5-tetrone, and
2-(4-chloro-2-fluorobenzyl)-[1,2,3,4-tetrahydropyrrolo[1,2-a]pyrazine-4-spiro-3'-pyrrolidine]-1,2',3,5'-tetrone, and enantiomers thereof having more potent aldose reductase inhibitory activity compared with the other enantiomer.

12. A pharmaceutical composition comprising an effective amount of a compound as set forth in claim 1, or a pharmaceutically acceptable salt thereof in admixture with a pharmaceutically acceptable carrier or diluent.

13. A pharmaceutical composition comprising an effective amount of a compound as set forth in claim 2, or a pharmaceutically acceptable salt thereof in admixture with a pharmaceutically acceptable carrier or diluent.

14. A pharmaceutical composition comprising an effective amount of a compound as set forth in claim 3, or a pharmaceutically acceptable salt thereof in admixture with a pharmaceutically acceptable carrier or diluent.

15. A pharmaceutical composition comprising an effective amount of a compound as set forth in claim 4, or a pharmaceutically acceptable salt thereof in admixture with a pharmaceutically acceptable carrier or diluent.

16. A pharmaceutical composition comprising an effective amount of a compound as set forth in claim 5 in admixture with a pharmaceutically acceptable carrier or diluent.

17. A pharmaceutical composition comprising an effective amount of a compound as set forth in claim 6 in admixture with a pharmaceutically acceptable carrier or diluent.

18. A pharmaceutical composition comprising an effective amount of a compound as set forth in claim 7 in admixture with a pharmaceutically acceptable carrier or diluent.

19. A pharmaceutical composition comprising an effective amount of a compound as set forth in claim 8 in admixture with a pharmaceutically acceptable carrier or diluent.

20. A pharmaceutical composition comprising an effective amount of the compound as set forth in claim 9 in admixture with a pharmaceutically acceptable carrier or diluent.

21. A pharmaceutical composition comprising an effective amount of the compound as set forth in claim 10 in admixture with a pharmaceutically acceptable carrier or diluent.

22. A pharmaceutical composition comprising an effective amount of a compound as set forth in claim 11 in admixture with a pharmaceutically acceptable carrier or diluent.

23. A method of the prevention and/or treatment of diabetic complications in mammals which comprises administering to said mammals in need of such prevention and/or treatment an effective amount of a compound as set forth in claim 1, or a pharmaceutically acceptable salt thereof.

24. A method of the prevention and/or treatment of diabetic complications in mammals which comprises administering to said mammals in need of such prevention and/or treatment an effective amount of a compound as set forth in claim 2, or a pharmaceutically acceptable salt thereof.

25. A method of the prevention and/or treatment of diabetic complications in mammals which comprises administering to said mammals in need of such prevention and/or treatment an effective amount of a compound as set forth in claim 3, or a pharmaceutically acceptable salt thereof.

26. A method of the prevention and/or treatment of diabetic complications in mammals which comprises administering to said mammals in need of such prevention and/or treatment an effective amount of a compound as set forth in claim 4, or a pharmaceutically acceptable salt thereof.

27. A method of the prevention and/or treatment of diabetic complications in mammals which comprises administering to said mammals in need of such prevention and/or treatment an effective amount of a compound as set forth in claim 5.

28. A method of the prevention and/or treatment of diabetic complications in mammals which comprises administering to said mammals in need of such prevention and/or treatment an effective amount of a compound as set forth in claim 6.

29. A method of the prevention and/or treatment of diabetic complications in mammals which comprises administering to said mammals in need of such prevention and/or treatment an effective amount of a compound as set forth in claim 7.

30. A method of the prevention and/or treatment of diabetic complications in mammals which comprises administering to said mammals in need of such prevention and/or treatment an effective amount of a compound as set forth in claim 8.

31. A method of the prevention and/or treatment of diabetic complications in mammals which comprises administering to said mammals in need of such prevention and/or treatment an effective amount of the compound as set forth in claim 9.

32. A method of the prevention and/or treatment of diabetic complications in mammals which comprises administering to said mammals in need of such prevention and/or treatment an effective amount of the compound as set forth in claim 10.

33. A method of the prevention and/or treatment of diabetic complications in mammals which comprises administering to said mammals in need of such prevention and/or treatment an effective amount of a compound as set forth in claim 11.

* * * * *